United States Patent [19]
Butler et al.

[11] Patent Number: 4,677,098
[45] Date of Patent: Jun. 30, 1987

[54] SUBSTITUTED DIHYDRO-1H-PYROLIZINE-3,5(2H,6H)-DIONES

[75] Inventors: Donald E. Butler, Holland; Anthony J. Thomas, Ann Arbor, both of Mich.

[73] Assignee: Warner-Lambert Company, Morris Plains, N.J.

[21] Appl. No.: 801,031

[22] Filed: Nov. 22, 1985

[51] Int. Cl.$^4$ .................. A61K 31/40; C07D 487/04
[52] U.S. Cl. .................................. 514/63; 514/413; 548/406; 548/453
[58] Field of Search ............... 548/406, 453; 514/63, 514/413

[56] References Cited

U.S. PATENT DOCUMENTS 4,372,966  2/1983  Butler .................................. 514/413
4,551,470 11/1985  Butler .................................. 514/413

Primary Examiner—Nicholas S. Rizzo
Assistant Examiner—Diana G. Rivers
Attorney, Agent, or Firm—Ronald A. Daignault

[57] ABSTRACT

Novel derivatives of substituted pyrrolizine diones, isomers, and pharmaceutically acceptable derivatives thereof, have therapeutic utility for reducing amnesia induced by electroconvulsive shock and for treating senility.

18 Claims, No Drawings

SUBSTITUTED DIHYDRO-1H-PYROLIZINE-3,5(2H,6H)-DIONES

BACKGROUND

Electroconvulsive shock, or ECS, is known to induce amnesia in a significant number of individuals subjected thereto. Studies on this type of amnesia in animals have resulted in the discovery of a number of compounds which at least ameliorate and, in some cases, virtually reverse, ECS-induced amnesia.

These compounds and their pharmaceutically acceptable formulations are also of value in treating senility.

INVENTION

A group of novel compounds have been shown to be effective in treating subjects suffering from ECS-induced amnesia. These novel compounds contain fused hetero-N-cyclic rings and conform to one of the general formula:

$$\text{(I)}$$

```
        H
H2C————C————CH2
 |      |     |
H2C     N    HC—OR
   \   / \   /
    C       C
    ‖       ‖
    O       O
``` wherein R is —H, —C(O)CH$_3$, —C(O)C(CH$_3$)$_3$, —C(O)C$_3$H$_7$, —C(O)CH$_2$C$_6$H$_6$, —Si(CH$_3$)$_2$C(CH$_3$)$_3$, —Si(C$_6$H$_5$)$_2$CH$_3$ or —Si(—C$_6$H$_5$)$_2$—C(CH$_3$)$_3$.

Compounds of formula (I) and pharmaceutically-acceptable formulations thereof, have utility as discussed above. Mixtures of compounds conforming to formula (I) can be used.

In addition, the compounds of the invention exist as dextro- and levorotatory optical isomers. These isomers as well as geometric isomers of structure (I) are contemplated as exhibiting similar biological activity. Mixtures of isomers, e.g., racemic mixtures, are useful.

ADVANTAGES

The compounds of the instant invention show promise as cognition activators and memory enhancers.

Furthermore, they are produced from well-known chemical intermediates, such as the methyl ester of 4-nitrobutanoic acid. The synthesis of this intermediate is described in U.S. Pat. No. 2,342,119 to H. A. Bruson. The disclosure of that patent is hereby incorporated by reference.

Other aspects and advantages of the invention will become apparent after a consideration of the following description and claims.

DESCRIPTION OF THE INVENTION

The invention provides a novel group of compounds and pharmaceutical formulations containing those compounds individually or in mixtures of cis- and trans- or other isomers. Generally, the subject compounds conform to formula (I) set out above.

The optical and geometric isomers of compounds of formula (I) and pharmaceutically-acceptable materials derived therefrom are also usefully biologically.

The subject compounds are new chemical entities and are 2-hydroxy-dihydro-1H-pyrrolizine-3,5(2H,6H)-dione and derivatives thereof. Generally, they are the dione, O-substituted derivatives thereof, and esters thereof.

Among the compounds and mixtures encompassed by the invention are: mixtures of cis- and trans-2-hydroxy-1H-pyrrolizine-3,5(2H,6H)-diones; mixtures of cis- and trans-2-acetoxy-dihydro-1H-pyrrolizine-3,5(2H,6H)-dione; mixtures of cis- and trans-2-butyroxy-dihydro-1H-pyrrolizine-3,5(2H,6H)-dione; mixtures of cis- and trans-dihydro-2-pivaloxy-1H-pyrrolizine-3,5(2H,6H)-dione; mixtures of cis- and trans-2-t-butyldiphenylsilyloxy-dihydro-1H-pyrrolizine-3,5(2H,6H)-dione; mixtures of cis- and trans-2-t-butyl-dimethylsilyloxy-dihydro-1H-pyrrolizine-3,5(2H,6H)-dione; mixtures of cis- and trans-2-carbobenzoxy-dihydro-1H-pyrrolizine-3,5(2H,6H)-dione and the like. Combinations containing one or several of these are contemplated.

Solvates and hydrates, as well as other pharmaceutically acceptable materials prepared from any of the compounds discussed above, are also within the scope of the invention. In general, the hydrated and/or solvated forms which use suitable solvents are equivalent to the anhydrous forms.

Where a plane of symmetry cannot be drawn through the molecular structure of the compounds or derivatives thereof, the compounds exist as d,l-isomers and the biological activity may reside in either or both of the isomers. In addition, because the parent structure dihydro-1H-pyrrolizine-3,5(2H,6H)-dione molecular is not flat but is bent down on each side of the nitrogen 7-alpha-carbon atom axis, the 2-substituent can be on either the exo- or the endo- side of the molecule.

The use of techniques conventionally used to treat or modify the subject compounds in order to render them more suitable for pharmaceutical use is contemplated.

PREPARATORY SCHEMES

The compounds of the invention are generally prepared using one or more of the following schemes. The compounds set forth are merely exemplary. Reasonable extrapolation to encompass the use of analogous reagents is within the purview of the skilled artisan.

Typical schemes include:

(1)

$$\text{MeOOC—(CH}_2\text{)}_3\text{—NO}_2$$
$$+ \xrightarrow{\text{PhNCO}}_{\text{Et}_3\text{N}}$$
$$\text{H}_2\text{C=C—COOMe}$$
$$\quad\quad\text{H}$$

```
                          H2,PtO2
MeOOC—(CH2)2—C————CH2    ———————>
              ‖    |
              N    C—COOMe
               \  /
                O
```

```
        H        OH        (1) NaOH
H2C————C—CH2—CH            (2) HCl
 |      |      |           ———————>
H2C     NH    COOMe        (3) Ac2O
   \   /
    C
    ‖
    O
```

```
        H
H2C————C————CH2
 |      |     |
H2C     N    HC—OAc
   \   / \   /
    C       C
    ‖       ‖
    O       O
```

Me=methyl,
Ph=phenyl,

Et=ethyl,
Ac=CH₃C(O)—
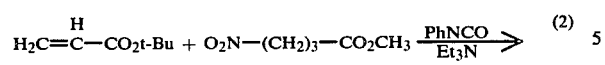 (2)
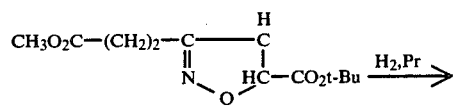
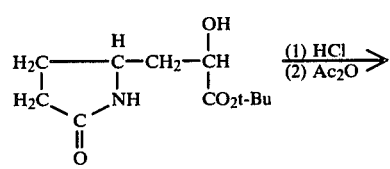
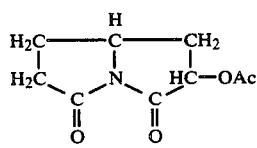
Ph=phenyl,
Et=ethyl,
Ac=CH₃C(O)—
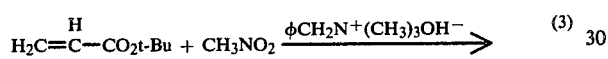 (3)
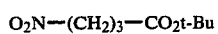
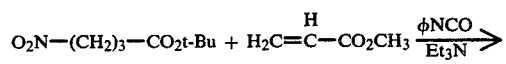
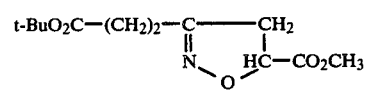
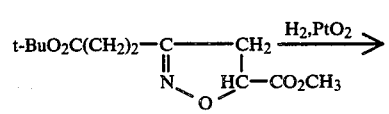
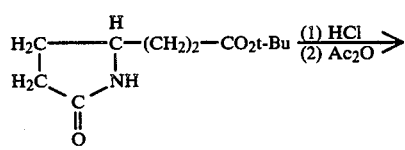
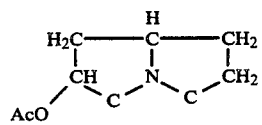
φ=phenyl,
et=ethyl,
t-Bu=tertiary butyl,
Ac=CH₃(C(O)—
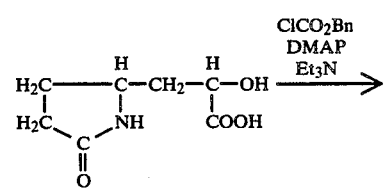 (4)
-continued
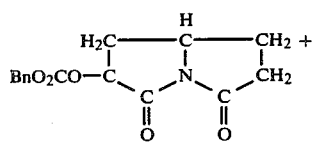
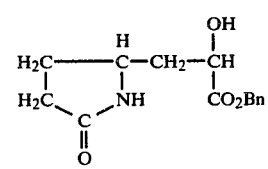
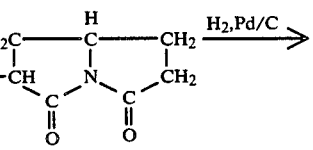
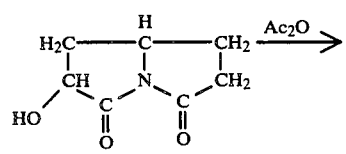
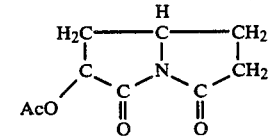
Bn=benzyl,
DMAP=4-dimethylaminopyridine,
Et=ethyl,
Ac=CH₃C(O)—
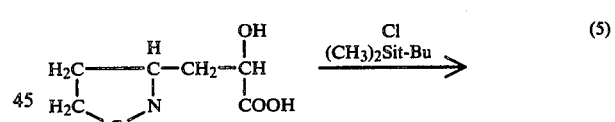 (5)
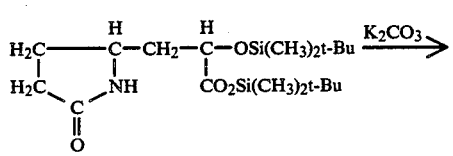
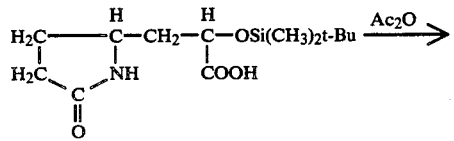
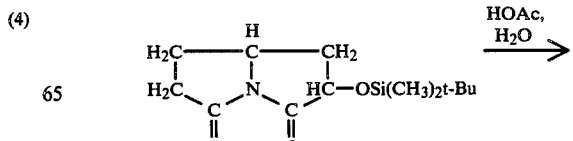

-continued

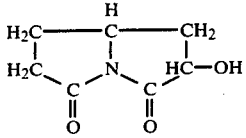

t-Bu=tertiary butyl,
HOAc=acetic acid

DOSAGE FORMS

The novel compounds disclosed herein, and pharmaceutically acceptable entities derived therefrom, are generally employed as active ingredients in compositions to be administered in unit dosage form.

Dosage forms will generally be of solid, semisolid, liquid or vaporous character. Useful dosage forms include, but are not limited to, tablets, capsules, lozenges, and pills as well as powders and aqueous and nonaqueous solutions and suspensions packaged in containers containing either one or some larger number of dosage units and capable of being subdivided into individual doses by such means as measurement into a teaspoon or other measuring device or container.

One or more suitable excipients, such as carriers, stabilizers, colorants, perfumes, flavoring agents, taste-making agents, and the like can be used in the subject compositions. Optionally, other active ingredients, i.e., one or more additional therapeutic agents, can be used in combination with the biologically active substances disclosed herein.

Useful carriers or diluents to be employed in compositives containing the subject compounds include a wide variety of materials. In general, any pharmaceutical diluent or carrier which does not significantly decrease the effectiveness of the active component(s) can be used.

Useful diluents include: sugars, such as lactose and sucrose; starches, such as corn starch and potato starch; cellulose derivatives, such as sodium carboxymethylcellulose, ethyl cellulose, methyl cellulose, and cellulose acetate phthalate; gelatin; talc; stearic acid; anhydrous magnesium stearate; vegetable oils, such as peanut oil, cottonseed oil, sesame oil, olive oil, corn oil, and oil of theobroma; propylene glycol; glycerine; sorbitol; polyethylene glycol; water; agar; alginic acid; as well as other compatible substances typically used in pharmaceutical formulations.

The compounds and derivatives disclosed herein can be incorporated into formulations to be administered via a variety of routes. For example, suitable salts and esters of the compounds of Formula I or the compounds themselves can be used in parenteral formulations.

In some cases, it is advantageous to employ the active ingredient in solid, e.g., powder, form, which solid form is subsequently combined with a suitable medium, e.g., an isotonic solution, prior to administration. The use of conventional pharmaceutical excipients and other therapeutic agents in such a medium is contemplated.

When topical, e.g., transdermal, administration is desired, the use of one or more active ingredient(s) with one or more carriers, surfactants, penetration enhancers or the like is suggested. Likewise, formulations for buccal or rectal administration can be made.

Solutions or suspensions of the drugs encompassed by the instant disclosure can be administered orally via syrups, elixirs, lozenges, chewable materials, and the like.

Nasal administration can be carried out by combining the active ingredient(s) with a suitable carrier and using appropriate packaging.

The percentage of active ingredient in the foregoing compositions can be varied within wide limits. However, it is generally present in a concentration of at least 10% in a primarily solid composition and at least 2% in a primarily liquid composition. The most satisfactory compositions are those in which a much higher proportion of the active ingredient is present.

The compositions of the invention preferably contain from about 1 to about 500 mg, preferably from about 5 to about 100 mg, of the active ingredient per dosage unit so that the entire amount to be administered during a day can be made up from a reasonable number of dosage units.

The estimated mammalian dosage for a 70 kg subject is from about 1 to about 1500 mg/day about (0.014 mg to about 21.4 mg/kg of weight per day), preferably about 25 to about 750 mg/day (about 36 mg to about 10.7 mg/kg of weight per day), optionally administered in divided proportions. Human subjects are preferred.

EXAMPLE I

Preparation of cis- and trans-2-acetoxy-dihydro-1H-pyrrolizine-3,5(2H,6H)-dione

A solution of 3.74 g of 4-hydroxy-5-oxo-2-pyrrolidinepropanoic acid methyl ester and 5-oxo-alpha-hydroxy-2-pyrrolidinepropanoic acid methyl ester in 20 ml of 1N aqueous sodium hydroxide solution is heated to 60° C. for two hours. The reaction mixture is concentrated at reduced pressure and 20.4 g of acetic anhydride, 3.03 g of triethyl amine and 2.5 g of 4-dimethylaminopyridine are added. The resulting solution is heated at 90° C. for 16 hours. The solution is filtered and concentrated. Fifty cc of toluene are added and the mixture is reconcentrated. This operation is repeated five times and the resulting oil is chromatographed over $SiO_2$ (elution with chloroform:2-propanol; 97:3) to yield cis- and trans-2-acetoxy-dihydro-1H-pyrrolizine-3,5(2H,6H)-dione as a white solid with mp 88°–96° C. NMR (CDCl$_3$) and 5.53 (dd, ½H), 2.15 (d, 3H). IR (KBr) 2992, 1785, 1753, 1701, 1463, 1448, 1385, 1319, 1281, 1257, 1223.

EXAMPLE II

Preparation of cis- and trans-2-butyroxy-dihydro-1H-pyrrolizine-3,5-(2H,6H)dione.

A solution of 3.74 g of 4-hydroxy-5-oxo-2-pyrrolidinepropanoic acid methyl ester and 5-oxo-alpha-hydroxy-2-pyrrolidinepropanoic acid methyl ester in 20 ml of 1N aqueous sodium hydroxide solution is heated to 60° C. for six hours. The reaction mixture is concentrated at reduced pressure and 4.0 g of butyric anhydride, 20 ml of toluene, and 2.5 g of 4-dimethylaminopyridine are added. The resulting solution is heated at 90° C. for three hours. The solution is filtered and concentrated. Fifty cc of toluene are added and the mixture is reconcentrated. The chloroform soluble material is chromatographed over $SiO_2$ (elution with chloroform:2-methanol; 97:3) to yield cis- and trans-2-butyroxy-dihydro-1H-pyrrolizine-3,5(2H,6H)-dione as a white solid with mp 145°–152° C. NMR (CDCl$_3$) and 5.54 (m, ½H), 5.24 (m, ½H), 4.22 (m, 1H), 2.94–0.73 (m, 13H). IR (cm$^{-1}$) 2965, 2930, 2875, 1790, 1742, 1710, 1460, 1415, 1385, 1310, 1270.

EXAMPLE III

Preparation of cis- and trans-2-pivaloxydihydro-1H-pyrrolizine-3,5-(2H,6H)dione

A solution of 3.74 g of 4-hydroxy-5-oxo-2-pyrrolidinepropanoic acid methyl ester and 5-oxo-alpha-hydroxy-2-pyrrolidinepropanoic acid methyl ester in 20 mil of 1N aqueous sodium hydroxide solution is heated to 60° C. for two hours. The reaction mixture is concentrated at reduced pressure and 4.7 g of pivalic anhydride, 20 ml of toluene, and 2.5 g of 4-dimethylaminopyridine are added. The resulting solution is heated at 90° C. for 16 hours. The solution is filtered and concentrated. Fifty cc of toluene are added and the mixture is reconcentrated. This operation is repeated five times and the resulting oil is chromatographed over SiO$_2$ (elution with chloroform:2-methanol; 97:3) to yield cis- and trans-2-pivaloxy-dihydro-1H-pyrrolizine-3,5(2H,6H)-dione as a white solid with mp 75°–77° C. NMR (CDCl$_3$) and 4.13 (m, 1H), 3.54 (m, 1H), 2.57–1.05 (m, 6H), 1.50 (s, 9H). IR (cm$^{-1}$) 2945, 2875, 1780, 1750, 1710, 1590, 1510, 1435, 1355, 1255.

EXAMPLE IV

Preparation of cis- and trans-2-t-butyl-diphenylsilyloxy-dihydro-1H-pyrrolizine-3,5(2H,6H)-dione A solution of 5-oxo-alpha-hydroxy-2-pyrrolidinepropanoic acid (1.73 g), t-butyl-diphenylsilyl chloride (11 g), and imidazole (5.4 g) is allowed to stir in dimethylformamide (50 ml) for six hours at room temperature. The solution is diluted with water (100 mL) and extracted with diethyl ether (4×100 mL). The combined extracts are concentrated and the oil is dissolved in methanol (50 mL) and a 10% aqueous solution of potassium carbonate (50 mL) is added and the solution is stirred 18 hours. The solution is concentrated and washed with saturated brine (50 mL) and extracted with diethyl ether (4×75 mL). The combined extracts are dried and concentrated to an oil. The oil is dissolved in acetic anhydride (50 mL) and the solution is heated at 90° C. for two hours. The solution is filtered hot, concentrated, and the residue purified by chromatography on SiO$_2$ (elution with chloroform:methanol; 99:1) to yield cis- and trans-2-t-butyl-diphenyllsilyoxy-dihydro-1H)-pyrrolizine-3,5(2H,6H )-dione as a white solid with mp 155°–156° C. NMR (CDCl$_3$) and 7.60 (m, 10H), 4.66 (m, ½H), 4.40 (dd, 1H), 3.86 (m, ½H), 2.77–1.55 (m, 6H), 1.08 (s, 9H). IR (KBr) 3074, 2933, 1858, 1791, 1705, 1591, 1474, 1430, 1380, 1313, 1279.

EXAMPLE V

Preparation of cis- and trans-2-t-butyl-dimethylsilyloxy-dihydro-1H-pyrrolizine-3,5(2H,6H)-dione A solution of 5-oxo-alpha-hydroxy-2-pyrrolidinepropanoic acid methyl ester (5.6 g) in 1.0M sodium hydroxide solution (30 mL) is stirred at 60° C. for two hours. The solution is treated with 3.0M hydrochloric acid (10 mL) and concentrated at reduced pressure. The 5-oxo-alpha-hydroxy-2-pyrrolidinepropanoic acid is treated with t-butyldimethylsilyl chloride (18 g) and imidazole (14 g) in dimethylformamide (120 mL) at room temperature with stirring for 18 hours. Water (300 mL) is added and the solution is extracted with diethyl ether (3×400 mL). The combined extracts are dried and concentrated. The oil is dissolved in methanol and a 20% solution of potassium carbonate (100 ml) is added. The solution is stirred two hours at room temperature and concentrated. Brine (100 mL) is added and the solution is made strongly acidic with concentrated hydrochloric acid (10 mL). The solution is extracted with diether ether (3×200 mL), dried, concentrated, and the oil is dissolved in acetic anhydride (150 ml). Triethylamine (94.5 ml) is added and the solution is heated at 90° C. for two hours. The solution is filtered hot and concentrated. Toluene is added and the solution is reconcentrated. Chromatography on SiO$_2$ elution with chloroform:methanol; 97:3, yields cis- and trans-2-t-butyldimethylsilyloxy-dihydro-1H-pyrrolizine-3,5-(2H,6H)-dione as a white solid with mp 156°–158° C. NMR (CDCl$_3$) and 4.62 (m, ½H), 4.43 (m, 1H), 4.06 (m, ½H), 2.83–1.63 (m, 6H), 1.05 (s, 9H), 0.06 (s, 3H), 0.05 (s, 3H). IR (KBr) 2930, 2859, 1782, 1702, 1474, 1377, 1314, 1281.

EXAMPLE VI

Preparation of 2-Hydroxy-dihydro-1H-pyrrolizine-3,5(2H,6H)-dione

A solution of 2-t-butyldimethylsilyloxy-dihydro-1H-pyrrolizine-3,5(2H,6H)-dione (2.1 g) in acetic acid:water, 3:1 (18 ml) is stirred at 60° C. for six hours. The solution is cooled, concentrated, toluene added and the solution reconcentrated. The oil is triturated with anhydrous ethyl ether and filtered to yield 2-hydroxy-dihydro-1H-pyrrolizine-3,5(2H,6H)-dione as a white solid with mp 135°–140° C. NMR (CDCl$_3$) and 5.48 (m, 1H), 4.47 (m, 1H), 4.10 (b.s., 1H), 2.93–1.36 (m, 6H). IR 3310, 2860, 1770, 1710, 1655, 1410, 1372, 1307, 1275.

PREPARATION OF NEW STARTING MATERIALS

A. Preparation of 5-oxo-alpha-hydroxy-2-pyrrolidinepropanoic acid methyl ester A suspension of 40 g of 4,5-dihydro-5-methoxycarbonyl-3-isoxazolepropanoic acid methyl ester and 2.0 g of PtO$_2$ in 400 ml of methanol is placed under a hydrogen atmosphere with agitation. After H$_2$ absorption is complete, the solution is filtered and the solvent removed under reduced pressure to give an oil. The oil is triturated with anhydrous diethyl ether to yield 5-oxo-alpha-hydroxy-2-pyrrolidinepropanoic acid methyl ester as a white solid with mp 87°–90° C. NMR (CDCl$_3$) and 6.94 (s, 1H), 4.38 (m, 1H), 3.96 (d, 1H), 3.73 (m, 1H), 3.70 (s, 3H), 2.44–1.81 (m, 6H). Ir(KBr) 3330, 3200, 2980, 1734, 1696, 1436, 1416, 1400, 1382, 1362, 1313, 1297, 1246, 1212.

B. Preparation of 4-hydroxy-5-oxo-2-pyrrolidinepropanoic acid t-butyl ester A suspension of 40 g of 4,5-dihydro-5-t-butoxycarbonyl-3-isoxazole-propanoic acid methyl ester and 2.0 g of PtO$_2$/C in 400 ml of methanol is placed under a hydrogen atmosphere with agitation. After H$_2$ absorption is complete, the solution is filtered and the solvent removed under reduced pressure to give an oil. The oil is triturated with anhydrous diethyl ether to yield 4-hydroxy-5-oxo-2-pyrrolidinepropanoic acid t-butyl ester as a white solid with mp 94°–95° C. NMR (CDCl$_3$)

and 6.83 (s, 1H), 4.42 (m, 1H), 3.93 (s, 1H), 3.70 (m, 1H), 2.78–1.66 (m, 6H), 1.47 (s, 9H). IR (KBr) 3320, 2980, 1732, 1705, 1456, 1417, 1353, 1368, 1295, 1260, 1214.

C. Preparation of 5-oxo-alpha-hydroxy-2-pyrrolidinepropanoic acid t-butyl ester A suspension of 105 of 4,5-dihydro-5-methoxycarbonyl-3-isoxazolepropanoic acid t-butyl ester and 2.0 g of $PtO_2/C$ in 1 L of methanol is placed under a hydrogen atmosphere with agitation. After $H_2$ absorption is complete, the solution is filtered and the solvent removed under reduced pressure to give an oil. The oil is titurated with anhydrous diethyl ether and filtered to yield 5-oxo-alpha-hydroxy-2-pyrrolidinepropanoic acid t-butyl ester as a white solid with mp 110°–112° C. NMR ($CDCl_3$) and 6.38 (s, 1H), 4.13 (m, 1H), 3.87 (m, 1H), 3.27 (d, 1H), 2.47–1.60 (m, 6H), 7.53 (s, 9H). IR (KBr) 3460, 3245, 2978, 2938, 1723, 1686, 1426, 1392, 1372, 1318, 1277, 1256, 1209.

D. Preparation of 5-oxo-alpha-hydroxy-2-pyrrolidinepropanoic acid 5-oxo-alpha-hydroxy-2-pyrrolidinepropanoic acid, methyl ester (1.87 g), and Amberlite (IR—120 H+) (1.9 g) in 20 ml of water is warned at 60° C. for 36 hours, filtered, and the solvent removed under reduced pressure. The resulting solid is washed with ethyl acetate and filtered to yield 5-oxo-alpha-hydroxy-2-pyrrolidinepropanoic acid. NMR ($DMSO_{D6}$) and 7.89 (d, J=11 Hz, 1HO, 5.35 (bs, 1H), 3.99 (m, 1HO, 3.44 (m, ½H), 3.30 (m, ½H), 2.48–1.21 (m, 6H). IR ($cm^{-1}$) 3370, 3280, 2940, 1694, 1355, 1213, 1120.

E. Preparation of 4-hydroxy-5-oxo-2-pyrrolidine-propanoic acid

4-Hydroxy-5-oxo-2-pyrrolidinepropanoic acid t-butyl ester (1.87 g) and trifluoracetic acid (1.2 g) in 10 ml of N,N-dimethylformamide was heated at 100° C. until disappearance of starting material by thin layer chromatography. After concentration under reduced pressure, the resulting solid is washed with acetone and filtered to give 4-hydroxy-5-oxo-2-pyrrolidinepropanoic acid with mp 129°–132° C. NMR ($DMSO_{D6}$) and 12.14 (s, 1H), 7.96 (d, J=5 Hz, 1H), 5.37 (m, 1H), 4.00 (m, 1H), 2.60–1.09 (m, 6H). IR ($cm^{-1}$) 3420, 3080, 2030, 2920, 1698, 1494, 1387, 1284.

F. Preparation of 5-oxo-alpha-hydroxy-2-pyrrolidinepropanoic acid benzyl ester 5-oxo-alpha-hydroxy-2-pyrrolidinepropanoic acid (1.1 g), triethylamine (1.2 g), N-N-dimethylaminopyridine (1.5 g), and benzyl chloroformate (17 g) in 40 ml tetrahydrofuran is heated at reflux for 16 hours. After cooling and filtering off the triethylamine-hydrochloride, the solution was concentrated and chromatographed on $SiO_2$ (elution with methanol:chloroform; 3:97) to yield 5-oxo-alpha-hydroxy-2-pyrrolidinepropanoic acid, benzyl ester mp 95°–96° C. NMR ($CDCl_3$) and 7.37 (s, 5H), 7.93 (d, 1H), 5.40 (s, 1H), 1.70 (m, 2H). IR (KBr) 3330, 3200, 1733, 1691, 1497, 1456, 1389, 1351, 1287, 1216.

G. Preparation of 4-nitrobutanoic acid t-butyl ester

To a stirred solution of 226 g (3.7 moles) of nitromethane and 5 g of aqueous 40% Triton B in 35 ml of t-butyl alcohol was added dropwise 56.7 g (0.53 moles) of t-butylacrylate. The reaction was cooled with an ice bath thought the reaction did not warm considerably. After stirring at room temperature for 18 hours, the solution was diluted with diethyl ether (500 ml) and washed with sat $NH_4Cl$ solution (2×200 ml). After drying over $MgSO_4$, the solution was concentrated in vacuo and distilled.

Fraction 1
56–63 C. 0.15 mm 34.6 g 34% [4-nitrobutanoic acid t-butyl ester]

Fraction 2
142–148 C. 0.05 mm 19.6 g 12% [4-nitroheptanedioic acid di-t-butylester]

Fraction 1
NMR($CDCl_3$) 4.50 (t, J=6H2, 2H), 2.40 (m, 4H), 1.43 (s, 9H)
IR ($cm^{-1}$) 2975, 2940, 1736, 1555, 1483, 1460, 1440

Fraction 2
NMR($CDCl_3$) 4.57 (m, 1H), 2.16 (m, 8HO), 1.46 (s, 9H),
IR ($cm^{-1}$) 2981, 2938, 1731, 1554, 1458, 1425, 1395, 1370

H. Preparation of 4,5-Dihydro-5-(methoxycarbonyl)-3-isoxazolepropanoic acid methyl ester A solution of 23.8 g of 4-nitrobutyric acid methyl ester (made in accordance with Bruson, U.S. Pat. No. 2,342,119) 39.6 g of methyl acrylate, 0.2 g triethyl amine in 200 ml of toluene is stirred and treated dropwise with 23.8 g of phenyl isocyanate. The mixture is stirred for 72 hours at room temperature and heated at 90° C. for two hours. The mixture is cooled, filtered to remove the diphyl urea, and concentrated under reduced pressure. The resulting oil is chromatographed on $SiO_2$ (elution with hexane:ethyl-acetate; 75:25) to yield 4,5-dihydro-5-(methoxycarbonyl)-3-isoxazolepropanoic acid methyl ester as a colorless oil. NMR ($CDCl_3$) and 4.93 (t, J=9 Hz, 1H), 3.72 (s, 3H), 3.63 (s, 3H), 3.20 (d, J-9 Hz, 2H9, 2.61 (s, 4H). IR (KBr) 2956, 2851, 1739, 1632, 1439, 1367, 1340, 1215. IR ($cm^{-1}$).

I. Preparation of 4,5-dihydro-5-(methoxycarbonyl)-3-isoxazolepropanoic acid t-butyl ester A solution of 18.9 g of 4-nitrobutyric acid t-butyl ester, 8.6 g of methyl acrylate, 0.2 g triethyl amine in 200 ml of toluene is stirred and treated dropwise with 27.4 g of phenyl isocyanate. The mixture is stirred for 72 hours at room temperature and heated at 90° C. for two hours. The mixture is cooled, filtered to remove the diphenyl urea, and concentrated under reduced pressure. The resulting oil is chromatographed on $SiO_2$ (elution with hexane:ethylacetate; 75:25) to yield 4,5-dihydro-5-(methoxycarbonyl)-3-isoxazolepropanoic acid t-butyl ester as a colorless oil. NMR ($CDCl_3$) and 5.00 (t, J=9 Hz, 1H), 3.77 (s, 3HO, 3.28 (d, J=9 Hz, 2H), 2.58 (s, 4H), 1.42 (s, 9H). IR ($cm^{-1}$) 2955, 2910, 1728, 1545, 1437, 1385, 1370, 1340, 12155, 1215.

J. Preparation of 4,5-dihydro-5-(t-butoxycarbonyl)-3-isoxazolepropanoic acid methyl ester A solution of 105 g of 4-nitrobutyric acid methyl ester (Bruson U.S. Pat. No. 2,342,119), 64 g of t-butyl acrylate, 1 ml triethyl amine in 200 ml of toluene is stirred and treated dropwise with 137 g of phenyl isocyanate. The mixture is stirred for 72 hours at room temperature and heated at 90° C. for two hours. The mixture is cooled, filtered to remove the diphenyl urea, and concentrated under reduced pressure. The resulting oil is chromatographed on elution with hexane:ethyl-acetate; 75:25) to yield 4,5-dihydro 5-(t-butoxycarbonyl)-3-isoxazolepropanoic acid methyl ester as a colorless oil. NMR (CDCl$_3$) and 4.87 (t, J=9 Hz, 1H), 3.70 (s, 3H), 3.20 (d, J=9 Hz, 2HO, 2.67 (s, 4H), 1.47 (s, 9H). IR (cm$^{-1}$) 2970, 1740, 1600, 1556, 1445, 1396, 1373, 1340, 1300, 1262, 1230.

EFFECTIVENESS AGAINST ECS-INDUCED AMNESIA

The effectiveness of the aforementioned compounds is determined by a test designed to show a compound's ability to reverse amnesia produced by electroconvulsive shock. The test is fully described in U.S. Pat. No. 4,145,347, which is herein incorporated by reference. The only differences between the test set out in the patent and the instant test being that the test compounds in the present instance are administered orally and the length of the electroconvulsive shock is 1.0 seconds in duration.

The following criteria are used in interpreting the percent of amnesia reveral scores: 40 percent or more (active=A), 25 to 39 percent (borderline=C) and 0 to 24 percent (inactive=N).

The percent of amnesia reversal of orally administered cis- and trans-2-acetoxy-dihydro-1H-pyrrolizine-3,5(2H,6H)-dione follows:

| Amnesia Reversal % mg/kg | | |
|---|---|---|
| 1 | 10 | 100 |
| 50 (A) | 14 (N) | 60 (A) |

Reasonable variations, such as those which would occur to a skilled artisan, can be made herein without departing from the scope of the invention.

We claim:

1. A compound of the formula:

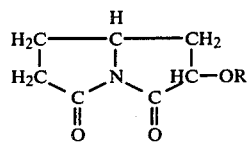

wherein R is —H, —C(O)CH$_3$, —C(O)C(CH$_3$)$_3$, —C(O)C$_3$H$_7$, —C(O)OCH$_2$C$_6$H$_6$, —Si(CH$_3$)$_2$C(CH$_3$)$_3$, Si(C$_6$H$_5$)$_2$CH$_3$, or —Si(C$_6$H$_5$)$_2$C(CH$_3$)$_3$.

2. The compound of claim 1 wherein R is an acetoxy group.

3. A mixture of the cis- and trans-isomers of the compound of claim 2.

4. The compound of claim 1 wherein R is a 2-tertiary butyl dimethyl siloxy group.

5. A mixture of the cis- and trans-isomers of the compound of claim 4.

6. A pharmaceutical formulation containing an effective amount of the compound of claim 2.

7. A pharmaceutical formulation containing an effective amount of the mixture of claim 3.

8. A pharmaceutical formulation containing an effective amount of the compound of claim 4.

9. A pharmaceutical formulation containing an effective amount of the mixture of claim 5.

10. The compound of claim 1 wherein R is a butyroxy group.

11. A mixture of the cis- and trans-isomers of the compound of claim 10.

12. The compound of claim 1 wherein R is a 2-tertiary-butyl diphenyl-siloxy group.

13. A mixture of the cis- and trans-isomers of the compound of claim 12.

14. The compound of claim 1 wherein R is a hydrogen atom.

15. A mixture of the cis- and trans-isomers of the compound of claim 14.

16. A pharmaceutical formulation containing an effective amount of the compound of claim 10.

17. A pharmaceutical formulation containing an effective amount of the compound of claim 12.

18. A pharmaceutical formulation containing an effective amount of the compound of claim 14.